(12) United States Patent
Yazawa

(10) Patent No.: US 11,588,090 B2
(45) Date of Patent: Feb. 21, 2023

(54) INTEGRATED THERMOELECTRIC FILM BASED WOVEN POWER GENERATOR

(71) Applicant: Purdue Research Foundation, West Lafayette, IN (US)

(72) Inventor: Kazuaki Yazawa, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 17/011,968

(22) Filed: Sep. 3, 2020

(65) Prior Publication Data
US 2021/0098673 A1 Apr. 1, 2021

Related U.S. Application Data

(60) Provisional application No. 62/895,298, filed on Sep. 3, 2019.

(51) Int. Cl.
*H01L 35/10* (2006.01)
*H01L 35/32* (2006.01)
*D03D 15/52* (2021.01)

(52) U.S. Cl.
CPC ............ *H01L 35/10* (2013.01); *D03D 15/52* (2021.01); *H01L 35/32* (2013.01); *D10B 2401/04* (2013.01)

(58) Field of Classification Search
CPC ......... H01L 35/10; H01L 35/32; D03D 15/52; D10B 2401/04
See application file for complete search history.

(56) References Cited

U.S. PATENT DOCUMENTS

| | | | |
|---|---|---|---|
| 2013/0087180 A1* | 4/2013 | Stark | H01L 35/30 136/205 |
| 2015/0311421 A1* | 10/2015 | Jur | H01L 35/32 136/205 |
| 2018/0240956 A1* | 8/2018 | Yazawa | H01L 35/30 |

OTHER PUBLICATIONS

Textilemates.com, "IoT In Intelligent Mobile Health Monitoring System By Smart Textile," retrieved from the internet Aug. 27, 2020, available at www.technicaltextile.net/articles/iot-in-intelligent-mobile-health-monitoring-system-by-smart-textile-8337 (11 pages).

* cited by examiner

*Primary Examiner* — Tamir Ayad
(74) *Attorney, Agent, or Firm* — Maginot, Moore & Beck LLP

(57) ABSTRACT

A thermoelectric module includes two insulating substrates supporting a plurality of thermoelectric fingers. Each thermoelectric finger has alternating strips of n-type doped material and p-type doped material, wherein adjacent n-type doped strips and p-type doped strips are separated by and electrically coupled to conductive regions. The thermoelectric fingers run in a first direction and are spaced apart from each other. A plurality of holes in the insulating substrates are disposed between adjacent thermoelectric fingers, and area aligned with each other. A length of fabric yarn woven is in and out of substantially aligned holes in each substantially aligned set of holes.

11 Claims, 7 Drawing Sheets

INTEGRATED THERMOELECTRIC FILM BASED WOVEN POWER GENERATOR

This application claims the benefit of U.S. Provisional Patent Application Ser. No. 62/895,298, filed Sep. 3, 2019, the entirety of which is incorporated herein by reference.

FIELD OF THE INVENTION

The present invention relates generally to power generation, and more specifically, generating power from body heat.

BACKGROUND

Wearable electronics has become an increasing area of research and commercialization. Wrist-worn electronic devices can track heartrate and various levels of activity. Embedding clothing with biosensors allows for the gathering of even more comprehensive biometrics and/or environmental conditions from humans (and possibly other living things) while engaged in various activities. Many sensors have been developed that are both amenable to use on apparel, and which can communicate data wirelessly.

While wrist-worn electronic devices can include a battery for power, sensors embedded into clothing do not lend themselves well to battery power. In particular, if various wearable sensors are placed on different parts of the body, it is inconvenient to implement a battery at each location, and inconvenient to convey electricity from a central location to various dispersed sensors. While small coin cells can be used to limit bulkiness, such batteries nevertheless have a limited charge cycle that is correlated to size. A short charge cycle is disadvantageous because charging typically involves connecting the battery or batteries to an external charging device, or in some cases simply replacement of the battery.

There is a need, therefore, for a more convenient apparatus and method for providing power to wearable sensors that reduces one or more of the inconveniences associated with the use of batteries.

SUMMARY

At least some embodiments of the invention include a woven thermoelectric module that may be used to generate electric power from body heat. The woven thermoelectric module forms a type of flexible woven fabric that can be readily integrated into clothing, including but not limited to shirts or undergarments. The woven thermoelectric module touches the human skin (or otherwise harvests heat from human skin). The woven thermoelectric module, based on the principles of operation of thermoelectric devices, generates a current therefrom that that can be used to charge a battery or other storage device that harvests power, either directly, or indirectly through intervening circuitry. The power generated may also be used for other purposes other than charging a battery, such as directly powering a wireless sensor circuit.

A thermoelectric module includes two insulating substrates supporting a plurality of thermoelectric fingers. Each thermoelectric finger has alternating strips of n-type doped material and p-type doped material, wherein adjacent n-type doped strips and p-type doped strips are separated by and electrically coupled to conductive regions. The thermoelectric fingers run in a first direction and are spaced apart from each other. A plurality of holes in the insulating substrates are disposed between adjacent thermoelectric fingers, and area aligned with each other. A length of fabric yarn woven is in and out of substantially aligned holes in each substantially aligned set of holes.

The above described features and advantages, as well as others, will become more readily apparent to those of ordinary skill in the art by reference the following detailed description and the accompanying drawings.

DETAILED DESCRIPTION

Figure 1:
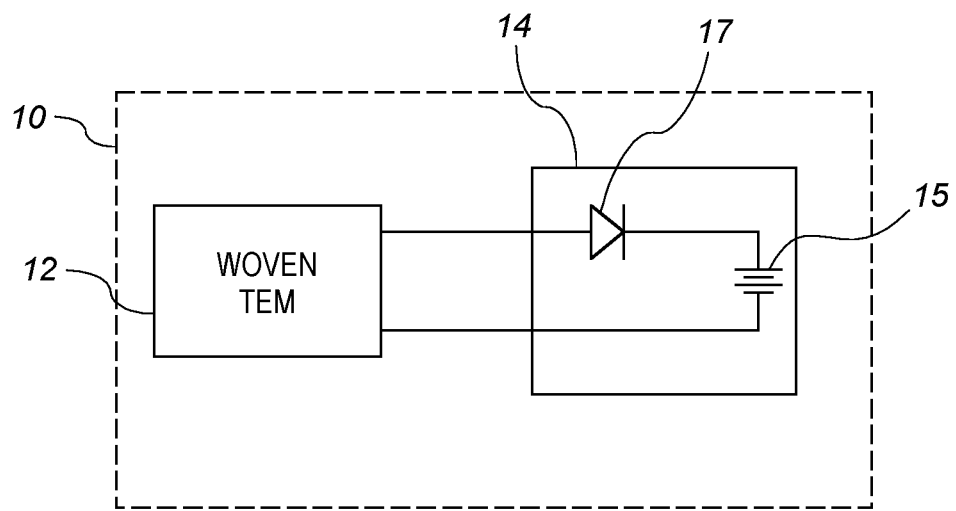
FIG. 1 shows schematic of a clothing article having a woven thermoelectric module according to a first embodiment.

FIG. 1 shows a schematic diagram of a first embodiment of an article of clothing 10 according to the invention. The clothing article 10 includes fabric, and at least in part, a woven thermoelectric module 12. The clothing article 10 also includes or at least supports a charging circuit 14. The charging circuit is 14 is operably coupled to receive electrical energy from the woven thermoelectric module 12. The charging circuit 14 uses the received electrical energy to trickle charge an energy storage device 15. In operation, the when the clothing article 10 is worn by a person, not shown, the thermoelectric module 12 has one surface adjacent to and preferably at least sometimes touching the skin of the wearer, and an opposite surface facing away from that surface and the wearer. The body heat of the wearer exceeds that of the ambient environment, and the thermoelectric module 12 is configured such that heat difference between the two surfaces creates an electrical current, which is then conveyed to and used to charge the storage device 15. The storage device 15 may be used to power a load, not shown. Further details regarding examples of this arrangement are provided below.

Figure 2A:
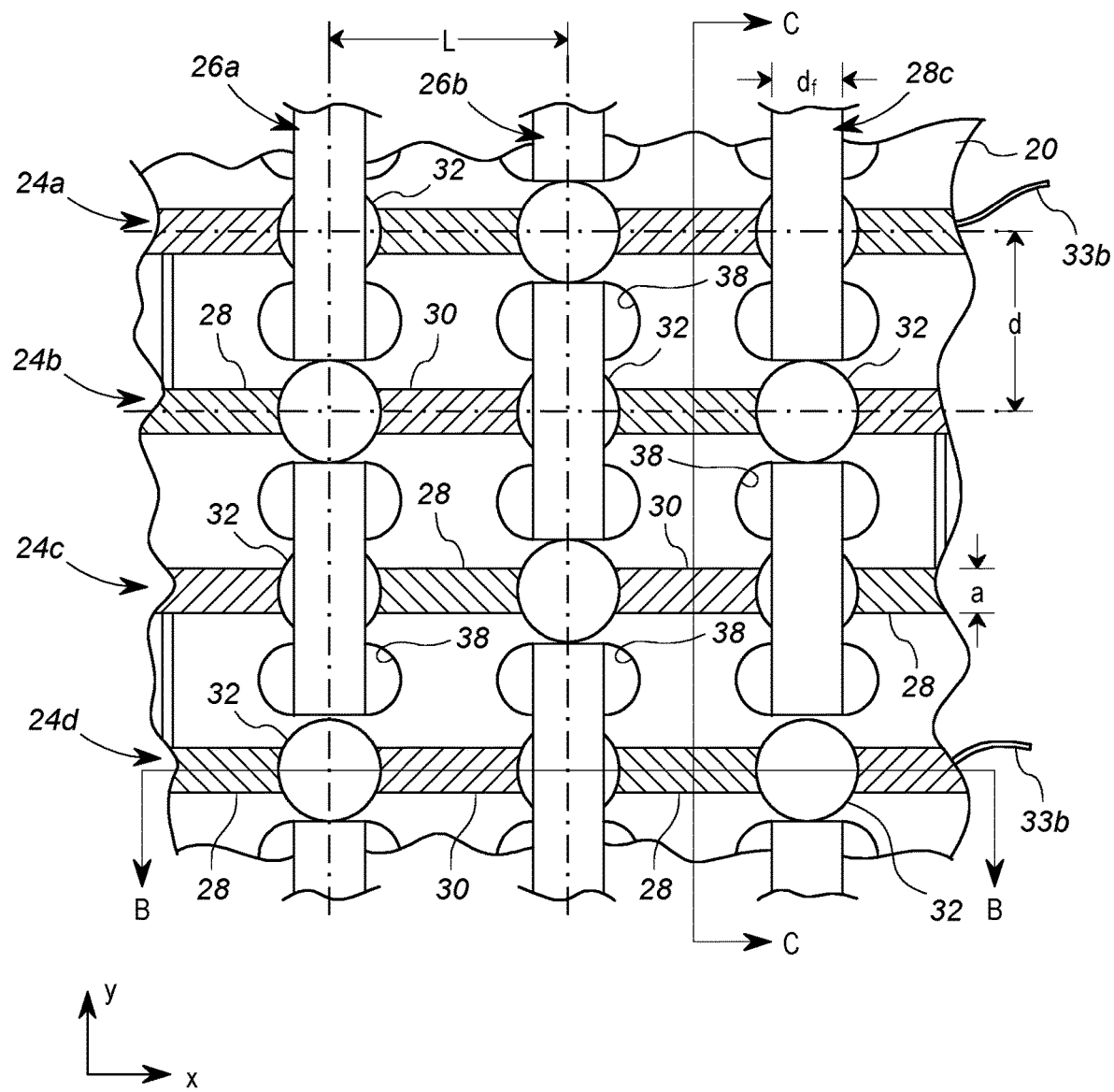
FIG. 2A shows a fragmentary representative top plan view of an embodiment woven thermoelectric module that may be used in the clothing article of FIG. 1, with the top insulating substrate removed for clarity of exposition.
Figure 2B:
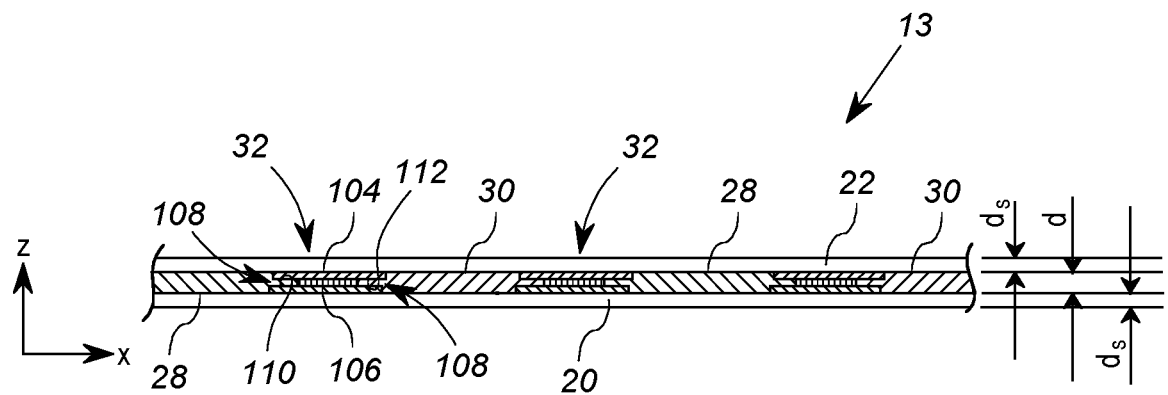
FIG. 2B shows a representative cutaway view of the woven thermostatic module taken along line B-B of FIG. 2A and including the top insulating substrate.
Figure 2C:
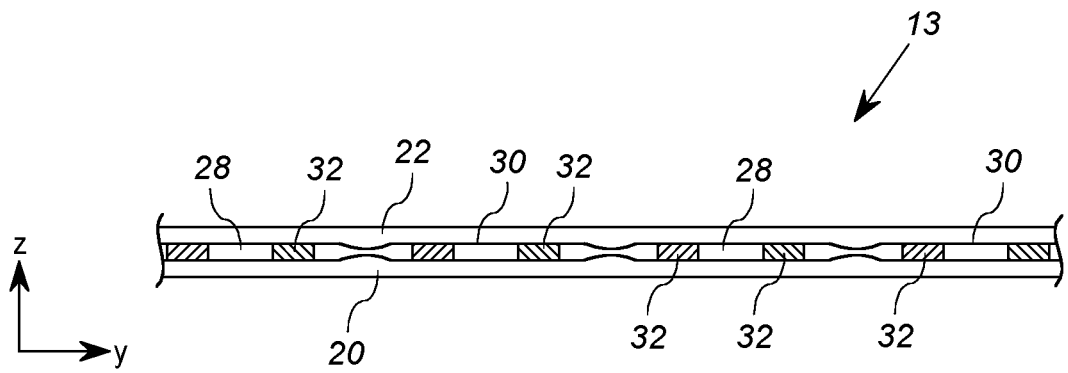
FIG. 2C shows a representative cutaway view of the woven thermostatic module taken along line C-C of FIG. 2A and including the top insulating substrate.
Figure 2D:
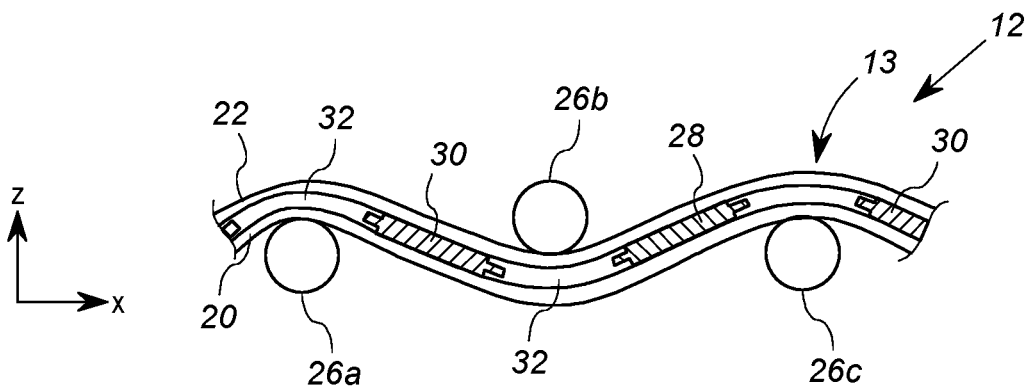
FIG. 2D shows a representative weaving pattern used in the thermoelectric module of FIG. 2A.

FIG. 2A shows a fragmentary representative top plan view of an exemplary embodiment of the woven thermoelectric module 12, with a top insulating substrate removed for clarity of exposition. FIG. 2D shows a representative cutaway view of the woven thermostatic module 12 taken along line B-B of FIG. 2A. The woven thermoelectric module 12 includes a flexible thermoelectric sheet element 13 and a plurality of lengths of yarn 26a, 26b, 26c. FIG. 2B shows a representative cutaway view of the thermoelectric sheet element 13 alone taken along line B-B of FIG. 2A with the lengths of yarn 26a, 26b and 26c removed. FIG. 2C shows a representative cutaway view of the thermostatic sheet element 13 taken along line C-C of FIG. 2A, also with the lengths of yarn 26a, 26b, and 26c removed.

With reference to FIGS. 2A-2D, the thermoelectric sheet element module 13 includes first and second insulating substrates 20, 22, a plurality of thermoelectric fingers 24a, 24b, 24c, 24d, a plurality of lengths of yarn 26a, 26b, 26c, and at least two terminal leads 33a, 33b. While the fragmentary view of FIG. 2A shows on four thermoelectric fingers 24a-24d, and three lengths of yarn 26a-26c, it will be appreciated that the thermoelectric sheet element 13 will have orders of magnitude more of each.

The first insulating substrate 20 is preferably a polymer film. In a first exemplary embodiment, the substrate 20 has a thickness $d_s$ of 80 μm. The second insulating substrate 22 may suitably be the same, not shown in FIG. 2A, but see FIGS. 2B and 2C. Other thicknesses may be used, but the substrates 20, 22 should be flexible and such that the sheet element 13 is capable of flexing to the weave pattern illustrated in FIG. 2D, and such that the woven thermoelectric module 12 can conform to the shape of the person wearing the garment 10. As will be discussed below in further detail, each of the substrates 20, 22 includes a plurality of holes 38. The plurality of thermoelectric fingers 24a, 24b, 24c and 24d are disposed between the two substrates 20, 22 in the z-direction, as shown in FIGS. 2B and 2C. The holes 38 may suitably be created as the lengths of yarn 26a, 26b and 26c are knitted in, or they may be created in a separate step.

Each of the plurality of thermoelectric fingers 24a, 24b, 24c, 24d includes alternating strips of n-type doped material 28 and p-type doped material 30. The material is a semiconductor material that has thermoelectric properties, such as bismuth telluride or bete. The adjacent n-type doped strips 28 and p-type doped strips 30 are separated by, and electrically coupled to, conductive regions 32. Each thermostatic finger 24a, 24b, 24c, 24d comprises a set of alternating p-type and n-type regions (strips 28, 30) connected in series by conductive regions 32. The thermostatic fingers 24a, 24b, 24c, and 24d are also connected in series to form a set of alternating p-type and n-type regions serially connected between the terminal leads 33a, 33b.

It will be noted that as discussed herein, the x-direction (rows) refers to a first direction depicted in FIG. 2A as the horizontal direction, the y-direction (columns) refers to a second direction depicted in FIG. 2A as the vertical direction, and the z-direction refers to a third direction, depicted in FIG. 2B as the vertical direction, and in FIG. 2C as the horizontal direction.

Each of the thermoelectric fingers 24a, 24b, 24c, 24d extends in the x-direction, and are parallel to each other (with respect to the x and y plane—they modulate in the z-direction, and are spaced apart in the y-direction. The thermoelectric fingers 24a, 24b, 24c, 24d thus form a plurality of spaced apart, parallel (in the x-y plane) rows of devices 28, 32, 30, 32, 28, and so forth. Although four fingers 24a, 24b, 24c, and 24d are shown by way of example, the woven TEM 12 will have many more similar fingers. Likewise, each finger 24a, 24b, 24c and 24d will have many more devices 28, 30, 32 in the same pattern. It will further be appreciated that at least some of the fingers 24a, 24b, 24c and 24d are connected to each other in series.

Preferably the conductive regions 32 are deposited metal contacts that have at least one surface that interfaces with n-type doped strips 28 along the x-direction, and at least one surface that interfaces with the p-type doped strips 30 along the x-direction. This increases the connectivity of the strips 28, 30 with the conductive regions 32. For example, as shown in FIG. 2B, each conductive region is defined as a plate having a top surface 104, a bottom surface 106, and a perimeter edge 108. The edge 108 includes a first interior channel 110 disposed between the top surface 104 and the bottom surface 106, and configured to receive a portion of the doped strip immediate adjacent thereto. The opposite side of the edge 108 includes a second interior channel 112 configured to receive a portion of the other doped strip immediately adjacent to the conductive region 32. For example, the conductive region $32_1$ includes a channel 110 that receives a portion or extension of the adjacent n-type doped strip 28, and includes a channel 112 that receives a portion or extension of the adjacent p-type doped strip 30.

As illustrated in FIG. 2B, the channels 110, 112 thereby defined a contact surface in the x-direction for greater interface between the doped strips 28, 30 and the conductive region 32. It will be appreciated that the channels 110, 112 need not have strictly horizontal walls, so long as they extend in a direction having a significant x-direction component sufficient to at least double the interface area as compared to a situation in which the edge 108 has no channels 1101, 112. Moreover, it will be appreciated that the channels 110, 112 may be formed as opposite sides of a continuous annular channel in the edge 108. Further, the conductive region need not be in the form of a round disc but may take other forms.

Referring again to FIG. 2A, the plurality of holes 38 in the first insulating substrate 20 and second insulating substrate 22 are disposed (in the x-y plane) between adjacent thermoelectric fingers, e.g. between fingers 24a and 24b, between fingers 24b and 24c, and between fingers 24c and 24d. The plurality of holes 38 between adjacent thermoelectric fingers substantially align with each other, for example, in the y-direction. As a result, each hole 38 is a part of a substantially aligned set of holes, aligned in this example in the y-direction (i.e. in columns).

Each length fabric yarn 26a, 26b, 26c is woven in and out in alternating fashion of substantially aligned holes 38 in each substantially aligned set of holes 38. In other words, each length of fabric yarn 26a, 26c is woven to pass alternatingly over and under, in the z-direction, adjacent thermoelectric fingers 24a, 24b, 24c, 24d. The length of fabric yarn 26b is woven to pass alternatingly under and over, in the z-direction, adjacent thermoelectric fingers 24a, 24b, 24c, 24d. Accordingly, every other length of fabric yarn 26 has the opposite over/under weaving sequence.

Thus, the thermoelectric fingers 24a, 24b, 24c and 24d and the lengths of fabric yarn 26a, 26b, 26c form an interlocking weave pattern, as shown in FIGS. 2A and 2D. The weave pattern in this embodiment is substantially perpendicular. However, it is possible that the weave pattern is no perpendicular, so long as the yarns 26a-26c and fingers 24a-24d extend in two different directions sufficiently to support a weave. It is possible that additional lengths of yarn or thermoelectric fingers may extend in yet another direction, and be weaved in.

As a result of the alternating yarn weave and the pattern of the fingers 24a, 24b, 24c and 24d, the thermoelectric module 10 aligns the higher temperature ends of all of the n-doped elements 28 and p-doped elements 30 on one side (in the z-direction) and aligns the lower temperature ends of all the elements 28, 30 on the other side (in the z-direction). To this end, as is known in the art, an n-doped thermoelectric element has a relationship between electrical current flow from end to end, and a temperature difference at each end. Thus, heat and cold applied to opposite ends of a thermoelectric element can cause the thermoelectric element to create a current, and applying a current to a thermoelectric element can cause a temperature difference to develop from end-to-end of the element.

More specifically, applying a current through a n-doped thermoelectric element causes a temperature gradient or difference between the first end of the element to the second end of the element, and applying a current through a p-doped element causes the opposite temperature gradient or difference between the first end of the element and the second end of the element. Conversely, an existing ambient temperature difference between the first end and second end of a thermoelectric element will cause the thermoelectric element to generate DC electrical current.

In the thermoelectric sheet 13 of FIGS. 2A and 2B, all the n-type doped elements 28 and p-typed doped elements are serially connected end to end. Accordingly, for a given current flow, the higher temperature ends of the elements 28, 30 and coupled to the same conductors 32, and the lower temperature ends of the elements 28, 30 are coupled to the same conductors 32. Furthermore, the conductors 32 alternate between being connected to the higher temperature ends and being connected to the lower temperature ends.

As shown in FIG. 2D, the weave pattern of the lengths of yarn 26a, 26b, 26c, disposes the conductors 32 alternatingly on one side or the other side (in the z-direction) of the woven thermoelectric module 12. Thus, for a given current flow, all of the higher temperature ends of the elements 28, 30 are disposed at or near one side (e.g. top) of the thermoelectric module 12, and all of the lower temperature ends of elements 28, 30 are disposed at or near the opposite side (e.g. bottom) of the thermoelectric module 12.

Conversely, with respect to the electrical energy generation properties of the module 12, if external conditions cause one side of the module 12 to have a higher temperature than the other side of the module 12, then all of the elements 28, 30 cooperate to generate current in the same direction between the terminals 33a and 33b. Thus, the weaving of the yarn 26a, 26b, 26c and the serial connection of the elements 28, 30 allow the thermoelectric module 12 to generate electrical current based on the temperature difference between the different sides of the module 12 in the z-direction. The yarn 26a, 26b, 26c provides the separation in the z-direction between the opposing ends of the elements 28, 30 to allow the heat difference on opposite sides to cause the elements 28, 30 to generate current. It will be appreciated that the yarn 26a, 26b, 26c may even be in the form of other kinds of thread that cause such separation.

Several factors can affect the energy generation, such as the number of elements 28, 30 in the module, the size of the elements 28, 30, the diameter of the yarn 26a, 26b, 26c, and spacing.

Figure 3:
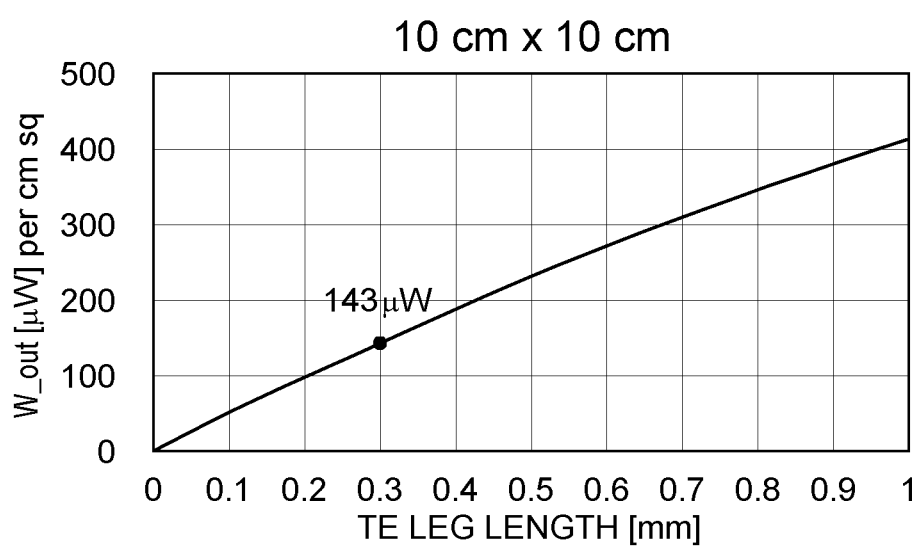
FIG. 3 shows a graph of the electrical power generated by the device an exemplary woven module having the design of the woven thermoelectric module of FIG. 2A.

FIG. 3 shows a graph of the output of energy per 10 cm$^2$ from the woven module 12 of FIGS. 2A-2D for given set of parameters, shown in table I below. The parameters include the spacing L of the yarn lengths, etc., the diameter $d_f$ of the thread in the yarn lengths 26, the width a of the doped strips 28, 30, the spacing P of the thermoelectric fingers 24, the thickness $d_s$ of the flexible insulating substrates 20, 22, and the thickness d of the elements 28, 30 and 32.

TABLE I

| |
| --- |
| L = 300 μm |
| P = 300 μm |
| a = 100 μm |
| d = 10 μm |
| $d_s$ = 80 μm |
| $d_f$ = 20-800 μm |
| Leg density = 1.00E+09 1/m$^2$ |
| cell area (P × L) = 9E−08 m$^2$ |
| Area of element (d × a) = 1.00E−09 m$^2$ |

Figure 4:
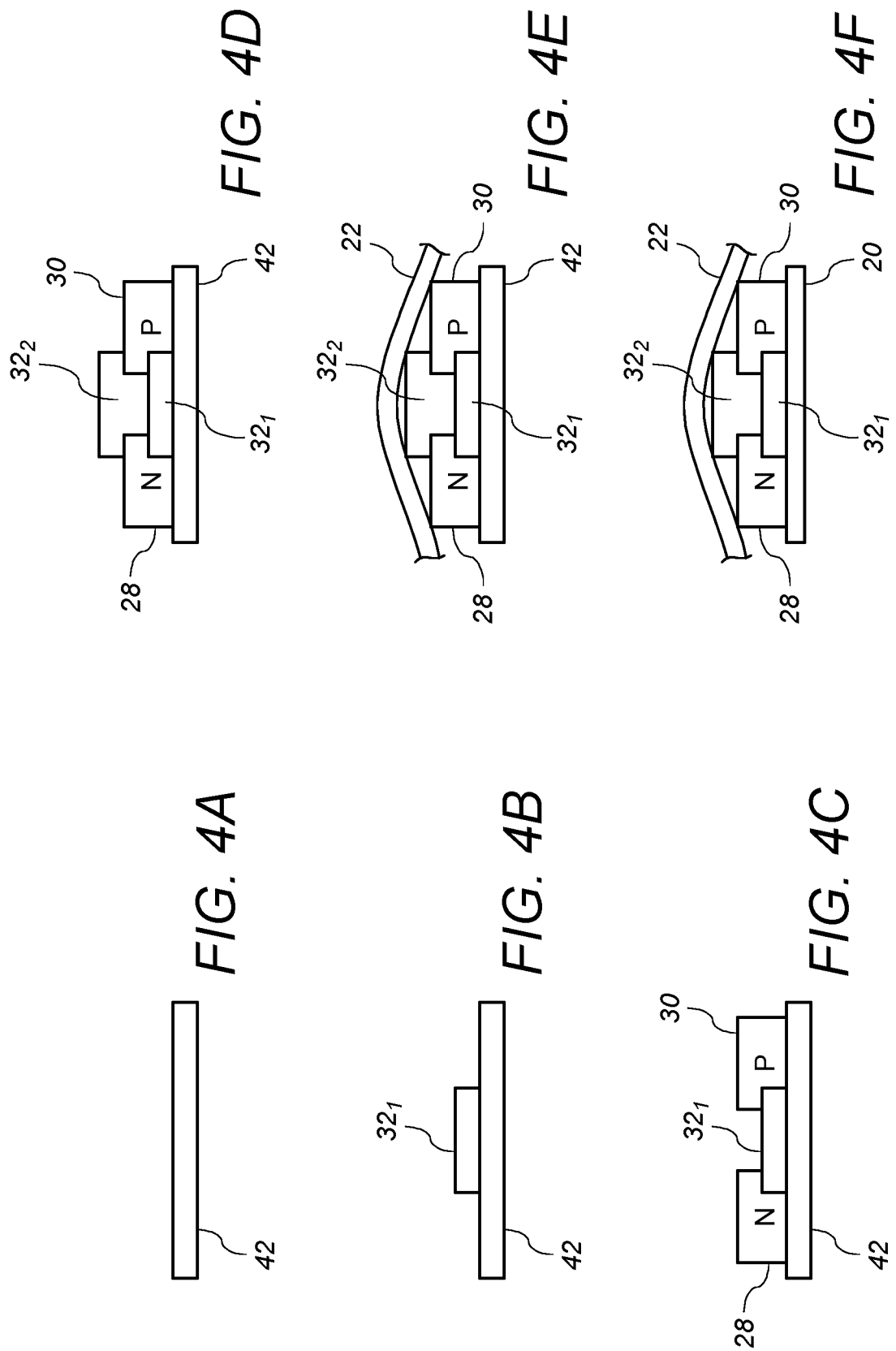
FIG. 4A shows a result of a first step of fabrication process of the woven thermoelectric module of FIG. 2A.
FIG. 4B shows a result of a second step of fabrication process of the woven thermoelectric module of FIG. 2A.
FIG. 4C shows a result of a third step of fabrication process of the woven thermoelectric module of FIG. 2A.
FIG. 4D shows a result of a fourth step of fabrication process of the woven thermoelectric module of FIG. 2A.
FIG. 4E shows a result of a fifth step of fabrication process of the woven thermoelectric module of FIG. 2A.
FIG. 4F shows a result of a sixth step of fabrication process of the woven thermoelectric module of FIG. 2A.

FIGS. 4A to 4F illustrate an exemplary fabrication process of the thermoelectric sheet 13 of the woven module 12. As shown in FIG. 4A a substrate 42 is provided. The substrate 42 is chosen as a sacrificial substrate that will be removed later, but provides a platform for the formation fingers 24a, 24b, etc.

In the next step, as shown in FIG. 4B, the lower parts $32_1$ of the conductive regions or metallized contacts 32 are formed on the substrate (in the grid pattern of FIG. 2A). This may be carried out by a known deposition technique for gold. Thereafter, as shown in FIG. 4C, the n-doped strips or regions 28 and p-doped strips or regions 30 are formed over the portions of the exposed substrate 42 in the pattern shown in FIG. 2A, the n- and p-doped regions 28, 30 also being partially formed on the lower parts $32_1$ of the contacts 32. The n-doped strips 28 and p-doped strips 30 are formed of a material with thermoelectric properties, such as $Bi_2Te_3$, or Bismuth Telluride.

Thereafter, as shown in FIG. 4D, the upper portions 322 of the metallizations 32 are formed over exposed lower portions $32_1$ and adjacent portions of adjacent n- and p-doped strips 28, 30, to complete the thermoelectric fingers 24a, 24b, 24c and 24d.

The second insulating substrate or polymer film 22 is than laminated onto the top of the thermoelectric fingers 24a, 24b, 24c and 24d, as shown in FIG. 4E. Thereafter, the substrate 42 is removed and the first insulating substrate 20 is laminated onto the side from which the substrate 42 was removed, resulting in the structure of FIG. 4F.

Although not shown in FIGS. 4A to 4F, the holes 38 are then cut into first and second insulating substrates 20, 22. The holes 38 are cut the pattern shown in FIG. 2A. Thereafter, the threads or lengths of yarn 26a, 26b, 26c are woven into and out of corresponding sets (e.g. columns) of the holes 38. As discussed further above, it will be appreciated that knitting the threads of yarn 26a, 26b, 26c itself may create the holes 38.

As discussed above, the thermoelectric fingers 24a, 24b, 24c and 24d are coupled in series between the contacts 33a, 33b. However, in some cases, groups of serially connected fingers may be coupled in parallel to other serially connected fingers.

As discussed above, the heat gradient across the thermoelectric module 12 causes a current flow in the alternating p-doped and n-doped strips 28, 30. The thermoelectric module 12 includes leads 33a, 33b, which delivers the current to the charging circuit 14. In this embodiment, the charging circuit 14 is shown a symbolically including a rectification device 17 that prevents the battery to be charged from draining into the module 12. It will be appreciated that those of ordinary skill in the art may devise a suitable circuit 14 to carry out the charging of the battery based on the currents provided by the thermoelectric module 12.

Figure 5:
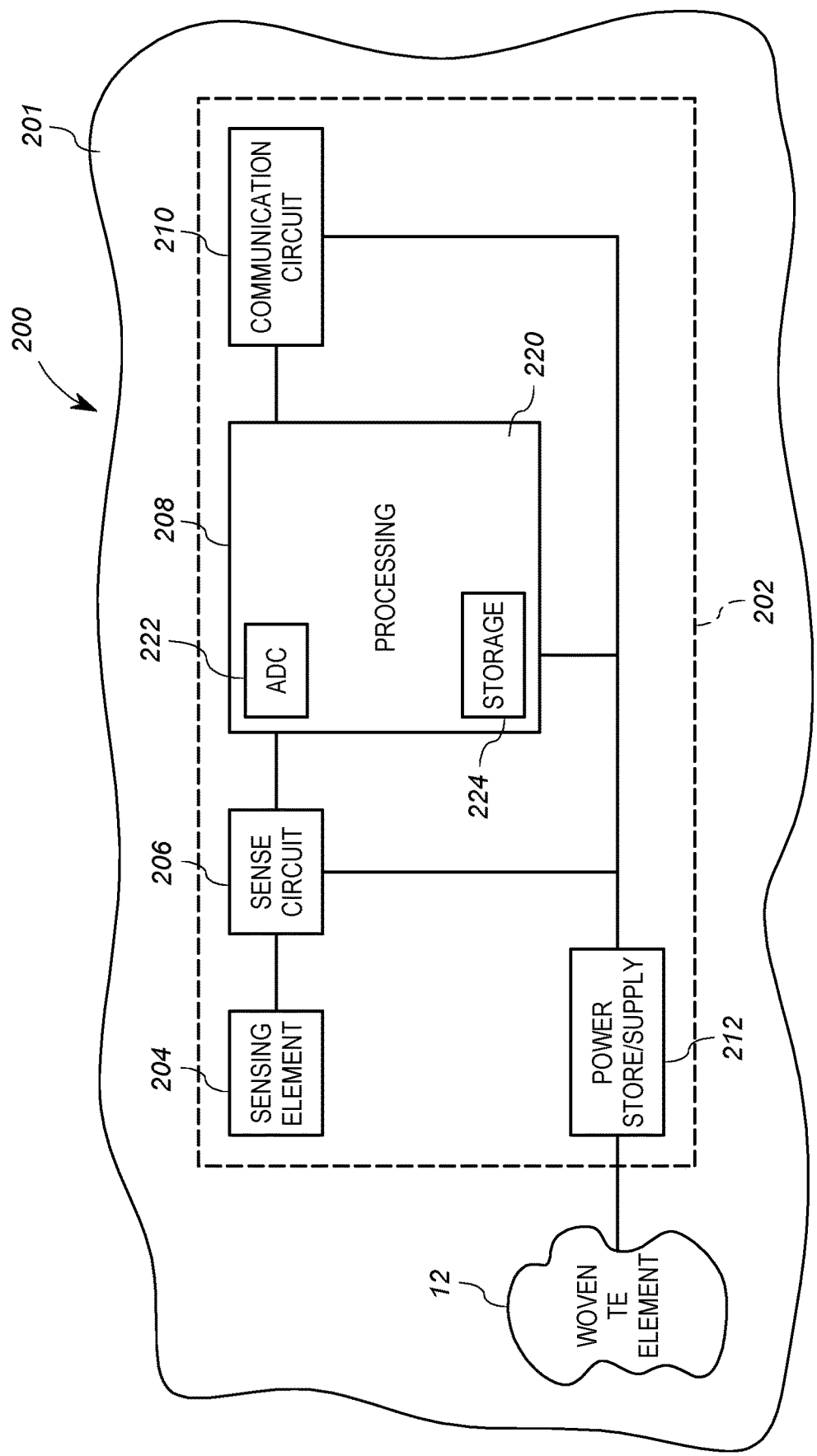
FIG. 5 shows a fragmentary schematic diagram of a second embodiment of a clothing article that incorporates the thermoelectric module of FIG. 2A.

FIG. 5 shows a schematic diagram of a second embodiment of a clothing article 200 according to at least one embodiment described herein, that may employ the thermoelectric module of FIG. 2A. The clothing article 200 includes a cloth apparel 201, at least one thermoelectric element 12 and at least one sensor 202. The cloth apparel 201 may suitably be any clothing item wearable by a human that is adjacent to skin. The cloth apparel 201 may take the form of a shirt, a brassiere, a sock or shoe, legwear, a glove or headwear. It will be appreciated that in other embodiments, the cloth apparel 201 may be designed for a non-human being.

In general, the sensor 202 is secured to the cloth apparel 201, and may be mounted thereon or incorporated or woven into the fabric of the cloth apparel 201 itself. Various devices for incorporating sensors with wearable clothing are known, and are described, for example, in "IoT in Intelligent Mobile Health Monitoring System by Smart Textile", published at https://www.technicaltextile.net. The sensor 202 is configured to measure a condition related to the living being and provide electrical sensor signals representative of the measured condition. The sensor 202 may suitably be a temperature sensor, pulse sensor, ECG sensor, accelerometer, among others. Such sensors may be based on MEMS technology, dry electrodes, diodes, and other known technologies. The sensor 202 is operably coupled to receive electrical energy from the thermoelectric element 12.

The thermoelectric module 12 is also supported on or incorporated in the cloth apparel 201. The thermoelectric module 12 may be attached, stitched or woven to the cloth apparel 201 adjacent to the sensor 202. The thermoelectric module 12 is incorporated into the cloth apparel 201 such that the thermoelectric module 12 is exposed to thermal energy from the body on one side thereof. For example, thermoelectric module 12 may suitably be attached to the underside of the cloth apparel such that the first insulating substrate 20 touches or is otherwise closest to skin at first location of the wearer's body, not shown, and the second insulating substrate 22 is further spaced apart from, and faces away from, the skin at the first location.

In such a position, and with simultaneous reference to FIG. 2A, the thermoelectric fingers 24a-24d are configured to generate electrical current from the difference in temperature between the first insulating substrate 20 and the second insulating substrate 22. The thermoelectric fingers 24a-24d are operably coupled to provide the electrical energy to the sensor 202. The sensor 202 may use the provided energy, at least in part, to directly or indirectly power electrical components in the sensor 202.

In the embodiment of FIG. 5, the sensor 202 includes a sensing element 204, a sense circuit 206, an integrated circuit 208, a communication circuit 210, and a power management circuit 212. The sensing element 204 is a device that changes a property based on the condition that it is sensing. For example, the sensing element 204 may be a photodiode that changes conductivity properties based on detected light levels, or a MEMs accelerometer that changes capacitance based on sensed acceleration. A wide variety of sensing elements suitably for wearable electronics are known.

The sense circuit 206 is a circuit that provides a biasing or probe signal to the sensing element 204 to detect the changed property. The biasing or probe signal creates a sensor electrical signal representative of a condition sensed by the sensor 204. The sense circuit 206 may also suitably include an amplifier and filter circuits, as is known in the art. The sense circuit 206 is operably coupled to provide the sensor electrical signal (which may be amplified and filtered) to the integrated circuit 208.

The integrated circuit 208 in this embodiment includes a processor 220, an A/D converter 222, and a memory 224. The A/D converter 222 is operably coupled to receive the sensor electrical signal and generate measurement data representative of the measured condition from the sensor electrical signal. The processor 220, which may be a microcontroller, general purpose microprocessor, or specialized processor, causes the data (or further processed data representative of the measured condition) in the memory 224. It will be appreciated, however, that the memory 224 may be operably connection to receive and store data representative of the measurement condition another way. For example, the sense circuit 206 itself may contain enough digitizing and filtering capability to generate the data for storage. It will be appreciated that the details of how measured condition information from the sensor 204 is stored in the memory 224 will depend on the specific needs of the implementation, and may take many forms. The memory 224 may in some cases be a FIFO type buffer, and in other cases a random access memory, by way of example.

The processor 220 is further operably coupled to the communication circuit 210. The communication circuit 210 is preferably a wireless circuit that is capable of transmitting data using Bluetooth or other known wireless protocols. The processor 220 is configured to cause the communication circuit 228 to transmit the condition data from the memory 224 to an external device, such as a portable computing device (e.g. smartphone). The communication circuit 210 may suitably be or include an RFID communication circuit, or another powered transmitter.

The power management circuit 212 is circuit configured to provide operating power to at least the integrated circuit 208 and the sense circuit 206. The power management circuit 212 in some embodiments also provides operating power to the communication circuit 210. The power management circuit 212 includes an energy storage device that is operably coupled to receive electrical energy from the thermoelectric fingers 24a-24d of the thermoelectric module 12 via electrodes 33a, 33b. (See FIG. 2A). The power management circuit 212 may also receive electrical energy from other sources on the cloth apparel 201 that can harvest energy from environmental conditions, such as a solar electrical element, not shown, or sources that harvest electrical energy from movement, or from incoming RF signals received by the communication circuit 210, for example.

The processor 220 may manage the operations of the sensor 202 to only periodically take measurements and/or transmit data, thereby allowing time for the power management circuit 212 to accumulate sufficient charge for operations.

Figure 6:
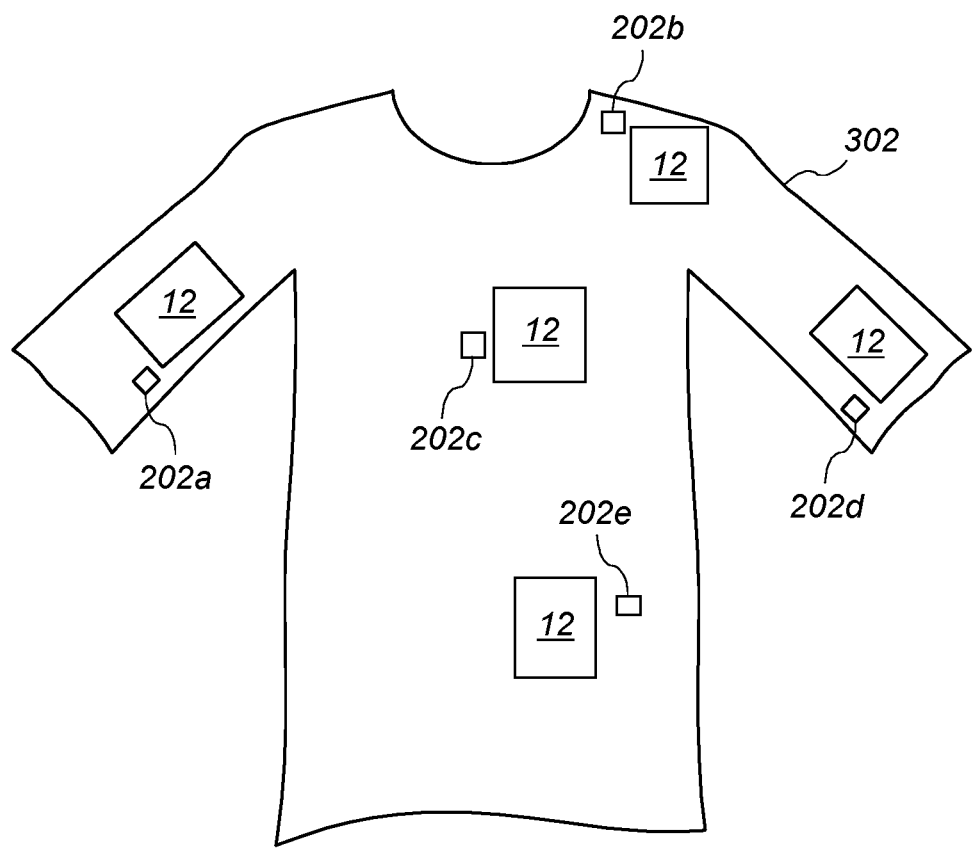
FIG. 6 shows a representative schematic diagram of the clothing article of FIG. 5 incorporating a plurality of sensors and woven thermoelectric modules.

One of the advantages using the woven thermoelectric module 12 as a power source for the sensor 202 is that it allows for the use of multiple, physically dispersed sensors on the clothing article 200. For example, FIG. 6 shows an exemplary embodiment of the clothing article 200 that includes a shirt 302 as the cloth apparel 201, a plurality of dispersed sensors 202a-202e, and a plurality of dispersed thermoelectric modules 12. Each of the thermoelectric modules 12 is disposed proximate to a corresponding one the sensors 202a-202e. This avoids having to run power conductors all throughout the shirt 302, which can create energy loss.

It will be appreciated that in some embodiments, the thermoelectric modules 12 may be formed the entire underside of the shirt 302, with multiple thermoelectric modules supported by the same first insulating substrate 20 and the same second insulating substrate 22, but having different electrode sets.

Thus, embodiments described herein provide a method of harvesting energy to use for powering biosensors that does not rely on changing batteries, or running long wires from a battery to various sensors.

Figure 7:
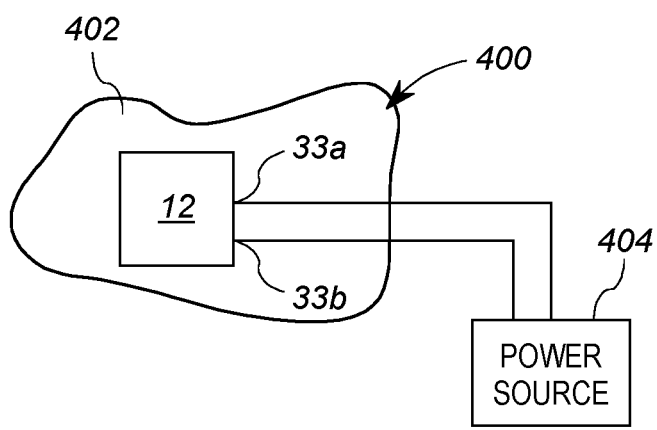
FIG. 7 shows a fragmentary schematic diagram of an alternative clothing article that includes a cloth apparel and the thermoelectrical module of FIG. 2A.

It will further be appreciated that the embodiment of FIG. 2A may be adapted to impart heat or cooling to select parts of the body as opposed to harvesting energy therefrom. In particular, FIG. 7 shows a fragmentary schematic diagram of a clothing article 400 that includes a cloth apparel 402 and the thermoelectric module 12. FIG. 7 also shows a power source 404 which may be mounted on the cloth apparel 402, or otherwise supported. The thermoelectrical module 12 may be mounted to the cloth apparel 402 in the same manner as described above in connection with FIGS. 5 and 6. However, in this case, the power source 404 provides electrical energy to the thermoelectrical module 12, instead of harvesting electrical energy therefrom.

In response to the electric energy in the form of DC current, the thermoelectric fingers 24a-24d generate a temperature gradient from the first insulating substrate 20 to the second insulating substrate 22. If the DC current is polarized one way, the first insulating substrate 20 generates heat and the second insulating substrate 22 is cooler. The first insulating substrate 20 can thus provide heating therapy to the skin against which it is disposed. If the DC current is polarized in the opposite way, the first insulating substrate 20 is the cooler side and the second insulating substrate 22 is warmer. The first insulating substrate 20 can thus provide cooling therapy to the skin against which it is disposed. It will be appreciated that such an embodiment would not require or use sensors. However, it could be possible to make a cloth article that has sensors and uses the thermoelectric module 12 selectably to provide power to the sensors, or to provide thermal therapy via a separate power source.

It will be appreciated that the above described embodiments are merely exemplary, and that those of ordinary skill in the art may readily devise their own implementations and modifications that incorporate the principles of the invention and fall within the spirit and scope thereof.

What is claimed is:

1. A clothing article, comprising:
    cloth apparel configured to be worn adjacent to skin of a living being;
    a woven thermoelectric module secured to the cloth apparel, the woven thermoelectric module including
        a thermoelectric sheet including a first substrate, a second substrate, and a plurality of thermoelectric fingers disposed between the first substrate and the second substrate, each thermoelectric finger comprising alternating strips of n-type doped material and p-type doped material, wherein adjacent n-type doped strips and p-type doped strips are separated by and electrically coupled to conductive regions, each of the plurality of thermoelectric fingers running in a first direction and spaced apart from each other, and
        a plurality of lengths of yarn woven through the thermoelectric sheet between adjacent fingers of the plurality of thermoelectric fingers; and
    at least one sensor secured to the cloth apparel, the sensor configured to measure a condition related to the living being and to provide electrical sensor signals representative of the measured condition, wherein the at least one sensor is operably coupled to receive electrical energy from the plurality of thermoelectric fingers.

2. The clothing article of claim 1, wherein a first sensor of the at least one sensor comprises:
    a sensing element and sense circuit operable to generate the electrical sensor signals;
    a communication circuit operably coupled to receive data representative of the electric sensor signals and transmit the data to a receiver, wherein the data representative of the electric sensor signals is representative of the measured condition.

3. The clothing article of claim 2, wherein the at least one sensor further comprises a power management circuit configured to receive the electrical energy from the thermoelectric fingers and provide bias power to at least the sense circuit and the communication circuit.

4. The clothing article of claim 2, further comprising a processor operably coupled to receive the electrical sensor signals and generate the data representative of the measured condition based on the received electrical sensor signals.

5. The clothing article of claim 1, wherein:
    the first direction is along an x-axis;
    each of the plurality of lengths of yarn run in a y-axis perpendicular to the x-axis; and
    each of the plurality of lengths of yarn is aligned with respective conductive regions of adjacent thermoelectric fingers and woven through the thermoelectric sheet such that adjacent conductive regions of each of the plurality of thermoelectric fingers are displaced in opposite directions along a z-axis perpendicular to the x-axis and to the y-axis.

6. A clothing article, comprising:
    cloth apparel configured to be worn adjacent to skin of a living being;
    a woven thermoelectric module secured to the cloth apparel, the woven thermoelectric module including
        a thermoelectric sheet including a first substrate, and a plurality of thermoelectric fingers disposed above the first substrate, each thermoelectric finger comprising alternating strips of n-type doped material and p-type doped material, wherein adjacent n-type doped strips and p-type doped strips are separated by and electrically coupled to conductive regions, each of the plurality of thermoelectric fingers running in a first direction and spaced apart from each other, and
        a plurality of lengths of yarn extending along a second direction perpendicular to the first direction, and
    at least one sensor secured to the cloth apparel, the sensor configured to measure a condition related to the living being and to provide electrical sensor signals representative of the measured condition, wherein
    the at least one sensor is operably coupled with the plurality of thermoelectric fingers to receive electrical energy from the plurality of thermoelectric fingers,
    the plurality of thermoelectric fingers includes a first, a second, and a third thermoelectric finger,
    the second thermoelectric finger is positioned between the first and third thermoelectric fingers, a first plurality of holes in the first substrate are disposed between the first and second thermoelectric fingers, a second plurality of holes in the first substrate are disposed between the second and third thermoelectric fingers, each of the first plurality of holes is substantially aligned with a respective one of the second plurality of holes along the second direction thereby defining a plurality of pairs of substantially aligned holes, each of the plurality of lengths of yarn is woven through a respective pair of the substantially aligned holes, between the first and second thermoelectric fingers, and between the second and third thermoelectric fingers.

7. The clothing article of claim 6, wherein a first sensor of the at least one sensor comprises:
- a sensing element and sense circuit operable to generate the electrical sensor signals;
- a communication circuit operably coupled to receive data representative of the electric sensor signals and transmit the data to a receiver, wherein the data representative of the electric sensor signals is representative of the measured condition.

8. The clothing article of claim 7, wherein the at least one sensor further comprises a power management circuit configured to receive the electrical energy from the thermoelectric fingers and provide bias power to at least the sense circuit and the communication circuit.

9. The clothing article of claim 7, further comprising a processor operably coupled to receive the electrical sensor signals and generate the data representative of the measured condition based on the received electrical sensor signals.

10. The clothing article of claim 6, wherein:
- a first of the plurality of lengths of yarn extends along the second direction through a first hole of the respective pair of the substantially aligned holes to a first location directly beneath the first substrate whereat the first of the plurality of lengths of yarn is spaced apart from the second thermoelectric finger by the first substrate; and
- the first of the plurality of lengths of yarn extends along the second direction through a second hole of the respective pair of the substantially aligned holes to a second location above the first substrate whereat the first of the plurality of lengths of yarn is not spaced apart from the second thermoelectric finger by the first substrate.

11. The clothing article of claim 10, the thermoelectric sheet further comprising:
- a second substrate located above the plurality of thermoelectric fingers, the second substrate including
  - a third plurality of holes substantially aligned with the first plurality of holes, and
  - a fourth plurality of holes substantially aligned with the second plurality of holes, wherein the first of the plurality of lengths of yarn is spaced apart from the second thermoelectric finger by the second substrate at the second location.

\* \* \* \* \*